United States Patent
King

(10) Patent No.: US 10,631,712 B2
(45) Date of Patent: Apr. 28, 2020

(54) SURGEON'S AID FOR MEDICAL DISPLAY

(75) Inventor: Timothy King, Goleta, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 473 days.

(21) Appl. No.: 13/289,554

(22) Filed: Nov. 4, 2011

(65) Prior Publication Data

US 2012/0209123 A1 Aug. 16, 2012

Related U.S. Application Data

(60) Provisional application No. 61/441,473, filed on Feb. 10, 2011.

(51) Int. Cl.
*A61B 1/00* (2006.01)

(52) U.S. Cl.
CPC .................... *A61B 1/0005* (2013.01)

(58) Field of Classification Search
CPC ........... A61B 5/0077; A61B 5/1128; A61B 2562/0219; A61B 5/7485; A61B 1/0005; A61B 6/00
USPC ........................................................ 600/476
See application file for complete search history.

(56) References Cited

U.S. PATENT DOCUMENTS

| | | | | |
|---|---|---|---|---|
| 4,216,589 A | * | 8/1980 | Beaver | 33/266 |
| 4,559,705 A | * | 12/1985 | Hodge et al. | 33/1 B |
| 5,099,846 A | | 3/1992 | Hardy | |
| 5,174,037 A | * | 12/1992 | Curtin | 33/512 |
| 5,517,278 A | * | 5/1996 | Takahara et al. | 396/374 |
| 5,573,492 A | * | 11/1996 | Dianna et al. | 600/117 |
| 5,627,915 A | * | 5/1997 | Rosser et al. | 382/219 |
| 5,836,869 A | * | 11/1998 | Kudo | A61B 1/00039 600/173 |
| 5,892,554 A | * | 4/1999 | DiCicco et al. | 348/584 |
| 6,014,472 A | * | 1/2000 | Minami et al. | 382/285 |
| 6,037,936 A | * | 3/2000 | Ellenby et al. | 715/764 |
| 6,057,833 A | * | 5/2000 | Heidmann et al. | 715/726 |
| 6,100,925 A | * | 8/2000 | Rosser et al. | 348/169 |
| 6,134,346 A | * | 10/2000 | Berman et al. | 382/163 |
| 6,359,644 B1 | | 3/2002 | Salvati | |

(Continued)

FOREIGN PATENT DOCUMENTS

| | | |
|---|---|---|
| EP | 2486847 A1 | 8/2012 |
| JP | H07184863 A | 7/1995 |
| WO | 2010088515 A1 | 8/2010 |

OTHER PUBLICATIONS

Adler et al., Overlay of Patient-Specific Anatomical Data for Advanced Navigation in Surgery Simulation, IWDE 2010 Magdeburg, Germany.*

(Continued)

*Primary Examiner* — Joanne M Hoffman
(74) *Attorney, Agent, or Firm* — Whitmyer IP Group LLC

(57) ABSTRACT

A system for identifying an area of interest on a surgical image, including a source of surgical image data, which may be a camera, an image processing unit, which may be a camera control unit, and a destination, which may be a display. The image processing unit is configured to receive the surgical image data and combine it with an overlay pattern for identifying an area of interest, which is then displayed on the display. The overlay may include a key with coordinates or labels. Properties of the overlay and the key may be customized and adjusted.

22 Claims, 14 Drawing Sheets

(56) References Cited

U.S. PATENT DOCUMENTS

| | | | |
|---|---|---|---|
| 6,414,696 B1* | 7/2002 | Ellenby et al. | 715/762 |
| 6,431,768 B1* | 8/2002 | Nakamura | 396/348 |
| 6,535,756 B1* | 3/2003 | Simon et al. | 600/424 |
| 6,630,937 B2 | 10/2003 | Kallergi et al. | |
| 6,636,254 B1 | 10/2003 | Onishi et al. | |
| 6,725,080 B2* | 4/2004 | Melkent et al. | 600/424 |
| 7,033,172 B2* | 4/2006 | Hansen et al. | 433/29 |
| 7,075,556 B1* | 7/2006 | Meier et al. | 345/629 |
| 7,366,934 B1 | 4/2008 | Narayan et al. | |
| 7,427,263 B2 | 9/2008 | Hoeg et al. | |
| 7,491,198 B2* | 2/2009 | Kockro | A61B 90/36 606/1 |
| 7,492,363 B2* | 2/2009 | Meier et al. | 345/419 |
| 7,590,335 B2* | 9/2009 | Kobayashi et al. | 396/50 |
| 7,607,079 B2 | 10/2009 | Reiner | |
| 7,782,384 B2* | 8/2010 | Kelly | 348/333.01 |
| 7,811,224 B2* | 10/2010 | Hale | A61B 1/0005 600/103 |
| 7,812,851 B2* | 10/2010 | Inakura | 345/629 |
| 7,849,024 B2* | 12/2010 | Lee | G06T 5/00 382/155 |
| 7,864,996 B2* | 1/2011 | Hemmer et al. | 382/128 |
| 7,907,166 B2* | 3/2011 | Lamprecht et al. | 348/43 |
| 7,949,965 B2* | 5/2011 | Tominaga | 715/764 |
| 8,073,528 B2* | 12/2011 | Zhao et al. | 600/424 |
| 8,213,788 B2* | 7/2012 | Soll et al. | 396/373 |
| 8,600,133 B2* | 12/2013 | Buelow et al. | 382/128 |
| 8,830,224 B2* | 9/2014 | Zhao et al. | 345/419 |
| 2002/0026093 A1* | 2/2002 | Ooyatsu | A61B 1/00188 600/118 |
| 2002/0049375 A1 | 4/2002 | Strommer et al. | |
| 2003/0069975 A1* | 4/2003 | Abjanic et al. | 709/227 |
| 2003/0114730 A1* | 6/2003 | Hale | A61B 1/00039 600/114 |
| 2004/0085455 A1* | 5/2004 | Silverstein | 348/211.4 |
| 2004/0127769 A1 | 7/2004 | Hale et al. | |
| 2005/0065435 A1* | 3/2005 | Rauch | A61B 34/73 600/427 |
| 2005/0075535 A1 | 4/2005 | Shapiro et al. | |
| 2005/0093889 A1* | 5/2005 | Sauer | G06T 19/003 345/633 |
| 2005/0146622 A9* | 7/2005 | Silverstein | 348/211.4 |
| 2005/0177026 A1 | 8/2005 | Hoeg et al. | |
| 2005/0187432 A1 | 8/2005 | Hale et al. | |
| 2006/0098112 A1* | 5/2006 | Kelly | 348/333.12 |
| 2006/0152516 A1* | 7/2006 | Plummer | G06F 19/321 345/538 |
| 2006/0217689 A1* | 9/2006 | Dick et al. | 606/4 |
| 2006/0257008 A1 | 11/2006 | Nolle et al. | |
| 2006/0258938 A1* | 11/2006 | Hoffman et al. | 600/424 |
| 2006/0259193 A1* | 11/2006 | Wang et al. | 700/245 |
| 2007/0073161 A1* | 3/2007 | Davidson | A61B 1/041 600/476 |
| 2007/0106282 A1* | 5/2007 | Lavallee | 606/1 |
| 2007/0147707 A1 | 6/2007 | Coste-Maniere et al. | |
| 2007/0156017 A1* | 7/2007 | Lamprecht | A61B 1/00193 600/102 |
| 2007/0269092 A1* | 11/2007 | Hill et al. | 382/131 |
| 2008/0004603 A1* | 1/2008 | Larkin | B25J 9/1692 606/1 |
| 2008/0015415 A1 | 1/2008 | Obata et al. | |
| 2008/0071142 A1 | 3/2008 | Gattani et al. | |
| 2008/0192116 A1* | 8/2008 | Tamir et al. | 348/157 |
| 2008/0303899 A1 | 12/2008 | Berci | |
| 2009/0036902 A1* | 2/2009 | DiMaio | A61B 34/10 606/130 |
| 2009/0087067 A1* | 4/2009 | Khorasani | 382/132 |
| 2009/0088634 A1* | 4/2009 | Zhao et al. | 600/427 |
| 2009/0088897 A1* | 4/2009 | Zhao et al. | 700/250 |
| 2009/0146950 A1 | 6/2009 | Maringelli | |
| 2009/0156895 A1* | 6/2009 | Higgins et al. | 600/104 |
| 2009/0171184 A1* | 7/2009 | Jenkins | A61B 5/7435 600/411 |
| 2009/0190808 A1 | 7/2009 | Claus | |
| 2009/0235570 A1* | 9/2009 | Sammut et al. | 42/122 |
| 2009/0248041 A1* | 10/2009 | Williams et al. | 606/130 |
| 2009/0271738 A1* | 10/2009 | Glaser-Seidnitzer | G06F 3/0482 715/821 |
| 2009/0274271 A1* | 11/2009 | Pfister | A61B 6/12 378/62 |
| 2009/0276725 A1 | 11/2009 | Glaser-Seidnitzer et al. | |
| 2010/0094085 A1* | 4/2010 | Yamamoto et al. | 600/109 |
| 2010/0160789 A1 | 6/2010 | Dilworth et al. | |
| 2010/0166323 A1* | 7/2010 | Zhao et al. | 382/218 |
| 2010/0168765 A1* | 7/2010 | Moraviec | 606/130 |
| 2010/0228249 A1* | 9/2010 | Mohr et al. | 606/41 |
| 2011/0135149 A1* | 6/2011 | Gefen | 382/103 |
| 2011/0137156 A1* | 6/2011 | Razzaque et al. | 600/424 |
| 2011/0141140 A1 | 6/2011 | Duhamel et al. | |
| 2011/0170755 A1* | 7/2011 | Buelow et al. | 382/128 |
| 2011/0235891 A1* | 9/2011 | Sonnemans et al. | 382/133 |
| 2012/0038744 A1* | 2/2012 | Naka | H04N 13/398 348/43 |
| 2012/0158019 A1* | 6/2012 | Tenney | A61B 17/32053 606/133 |
| 2012/0209123 A1 | 8/2012 | King | |
| 2013/0197357 A1* | 8/2013 | Green et al. | 600/424 |
| 2014/0037165 A1 | 2/2014 | King et al. | |
| 2014/0051986 A1* | 2/2014 | Zhao et al. | 600/424 |
| 2014/0055489 A1* | 2/2014 | Itkowitz et al. | 345/633 |
| 2014/0111623 A1* | 4/2014 | Zhao et al. | 348/47 |
| 2014/0142422 A1* | 5/2014 | Manzke et al. | 600/424 |
| 2014/0176661 A1* | 6/2014 | Smurro et al. | 348/14.06 |
| 2014/0267603 A1* | 9/2014 | Kerdok et al. | 348/43 |
| 2014/0275760 A1* | 9/2014 | Lee et al. | 600/102 |

OTHER PUBLICATIONS

Yang et al., Informatics in Radiology (infoRAD) Multimedia Extension of Medical Imaging Resource Center Teaching Files, RadioGraphics 2005; 25:1699-1708.*

European Search Report Application No. EP14166034 Completed: Aug. 25, 2014; dated Sep. 1, 2014 pp. 6.

European Search Report Application No. EP 14 18 8189 Completed: Mar. 19, 2015; dated Mar. 27, 2015 6 pages.

Canadian Office Action Application No. 2,766,595 dated May 3, 2015 Completed: Apr. 27, 2016 5 Pages.

European Office Action Application No. 14188189.6 Completed: Dec. 17, 2015 4 Pages.

European Office Action Application No. 12154966.1 Completed Date: Nov. 7, 2017 4 Pages.

U.S. Office Action U.S. Appl. No. 14/408,913 dated Jun. 1, 2018 17 pages.

European Office Action Application No. 14166034.0 Completed: Jul. 5, 2018 4 Pages.

U.S. Office Action U.S. Appl. No. 14/048,913 dated Dec. 13, 2018 19 Pages.

European Search Report Application No. EP 12 15 4966 Completed: May 31, 2012; dated Jun. 12, 2012 6 pages.

* cited by examiner

SURGEON'S AID FOR MEDICAL DISPLAY

CROSS REFERENCE TO RELATED APPLICATIONS

The present application claims the benefit under 35 U.S.C. § 119(e) of the U.S. Provisional Patent Application No. 61/441,473, filed on Feb. 10, 2011. The content of all prior applications is incorporated herein by reference.

FIELD OF THE INVENTION

The present invention relates to a system for displaying images from a surgical procedure. Specifically, the present invention relates to a method and apparatus for generating an overlay aid on images from a live surgical procedure.

BACKGROUND OF THE INVENTION

In modern medicine, treatments are being carried out more and more using technical imaging methods. By way of example, miniaturized cameras are inserted into the body of a patient, and the image taken by the camera is displayed to the physician on a monitor installed in his/her working area. In this way, the physician can, for example, examine an internal organ or a joint for diagnostic purposes and he/she can also carry out surgical operations in a minimally invasive fashion. By arranging a monitor in the working area of the physician, i.e. in the sterile area, the physician may track all the operations that he or she undertakes on the patient live on the monitor, the corresponding monitor image being picked up by the medical imaging system. Accordingly, during various types of minimally invasive surgeries, such as, endoscopic, arthroscopic and laparoscopic procedures, a surgeon is able to visibly examine the interior of an organ, joint or other anatomical structure while the surgeon is conducting the surgery.

Recent developments have resulted in systems incorporating various audiovisual devices to allow others in the surgical suite or located remotely therefrom who may be assisting or observing, to better monitor the surgical procedure. Accordingly, both still images and live video being acquired during the surgery can be output to various different monitors or recording devices both within, and outside of the surgical suite. Additionally, various devices have been incorporated into these systems to allow the surgeon, or other individuals assisting or observing, to utilize the imaging capabilities of the system in different ways, simultaneously or at different times, for a variety of different objectives.

Moreover, when there are multiple persons assisting in or observing a surgery, it is often necessary to call attention to or identify certain areas of interest within the patient's body shown on a live surgical monitor. For example, an instructor may wish to call attention to certain internal organs or structures, pathologies or procedures to students while observing a surgery. In addition, a supervising surgeon may direct the main practitioner to add more sutures in an area of interest.

In order to further improve communication during these surgical procedures, it is desired to have a method or device for calling attention to or identifying certain areas of interest displayed on the live surgical monitor. This would facilitate efficient and clear communication regarding a particular area of interest and diminish confusion, misunderstandings and misinterpretations.

Certain methods and devices have been tried to identify regions of interest on a live surgical monitor, including, use of a laser pointer or cursor or "circling" or annotating on a touch screen by the surgeon or assistants, or others assisting in or observing the surgery. These known methods have many disadvantages. First, the surgeon cannot operate a laser pointer or make indications on a touch screen while also safely performing the surgical procedure. Second, these known methods, including the use of a cursor, require the use of an additional hand, which the surgeon often cannot spare.

SUMMARY OF THE INVENTION

Against this background, it is an object of the present invention to provide a method and an apparatus for identifying regions of interest on images displayed on a live surgical monitor.

It is another object of the invention to provide such a method and apparatus in a simple and cost effective way.

It is another object of the invention that the image properties of the method and/or apparatus for identifying regions of interest be configurable and adjustable.

It is yet another object of the invention to enable a physician to configure and adjust the properties of image in and around an identified region of interest.

In accordance with one aspect of the invention, a configurable overlay pattern for identifying regions of interest on a surgical monitor. In another aspect, the areas of interest defined by the overlay pattern may be labelled with coordinates, such as numbers and/or letters, for ease of reference. If, for example, the overlay pattern is a grid, the rows and columns of the grid may be labelled with Cartesian coordinates. In accordance with another aspect of the invention, the properties of the surgical image in and/or around an identified region of interest may be adjusted. In accordance with a further aspect of the invention, the overlay pattern may be applied to displayed images recalled from an image archive. The applied overlay pattern may also be maintained on captured images that are subsequently saved to an archive.

Moreover, the novel method and apparatus have the advantage that the surgical image including the overlay pattern is directly available for further processing outside the sterile area. This further processing can include, for example, displaying on a remote training monitor and/or archiving in an electronic patient card file. The novel system therefore offers an extended field of application.

In one aspect, a system for identifying an area of interest on a surgical image, comprising a camera for generating surgical image data; a camera control unit receiving and processing said surgical image data from said camera; software executing on said camera control unit for applying an overlay pattern to said surgical image data; and a display controlled by said camera control unit for displaying said surgical image data and said overlay pattern, is provided. The system may also include a storage device for saving the surgical image data and the overlay pattern. The surgical image data may be video data, still frame data or combinations thereof. The overlay pattern itself may comprise a grid, crosshairs, quadrants, one or more hash marks, a circle or an oval and the pattern may be applied centered on the image as displayed or at the edges. A key for identifying one or more regions of the overlay pattern may also be provided. At least one property of the overlay pattern may also be adjustable, including brightness, contrast, opacity, resolution and color. The properties of the overlay may be adjusted via one or more a buttons located on said camera, via a touchscreen or via a voice recognition software executing on the camera control unit.

In another aspect, a system for identifying an area of interest on a surgical image, comprising a source of surgical image data; an image processing unit in communication with said source, the surgical image processing unit being configured to receive the surgical image data and combine it with an overlay pattern for identifying an area of interest; and a destination in communication with said image processing unit for receiving said surgical image data combined with said overlay pattern, is provided. The system may further include software executing on said image processing unit for combining said surgical image data with said overlay pattern. The source of image data, which may be video data, still frame data and combinations thereof, may be a camera, a storage medium, or a camera control unit. The destination may be a display, which may be configured to simultaneously display surgical image data from more than one source in combination with an overlay pattern, or a storage medium.

In yet another aspect, a method for identifying an area of interest on a surgical image, comprising providing a source of surgical image data; transmitting the surgical image data to a camera control unit from the source; combining said surgical image data with an overlay pattern in said camera control unit; transmitting said surgical image data combined with said overlay pattern to a display; displaying said surgical image data combined with said overlay pattern on said display, is provided. Software executing on said camera control unit for combining said surgical image data with said overlay pattern may also be provided. The method may also include the step of saving the surgical image data combined with said overlay pattern to a storage medium in communication with said camera control unit. The method may further comprise the steps of selecting a desired pattern, adjusting the source of image data such that an area of interest is located near a region of said overlay pattern, and identifying an area of interest in said surgical image data by referencing said overlay pattern.

It goes without saying that the features mentioned above and those yet to be explained below can be used not only in the combination respectively specified, but also in other combinations or on their own without departing from the scope of the present invention.

DETAILED DESCRIPTION OF THE INVENTION

The present invention provides a system 10 for identifying certain areas of interest in surgical image data by applying an overlay pattern, such as a Cartesian grid, crosshairs, quadrants, etc., on the surgical image. The overlay pattern allows a surgeon to then refer or call attention to areas of interest in the surgical image data by referencing the overlay pattern or a portion thereof. As will be discussed in detail below, the overlay may also include an key, which may include alphanumeric labels or coordinates, which may assist the surgeon in identifying the area or portion of the overlay to which he/she is referring.

Figure 1:
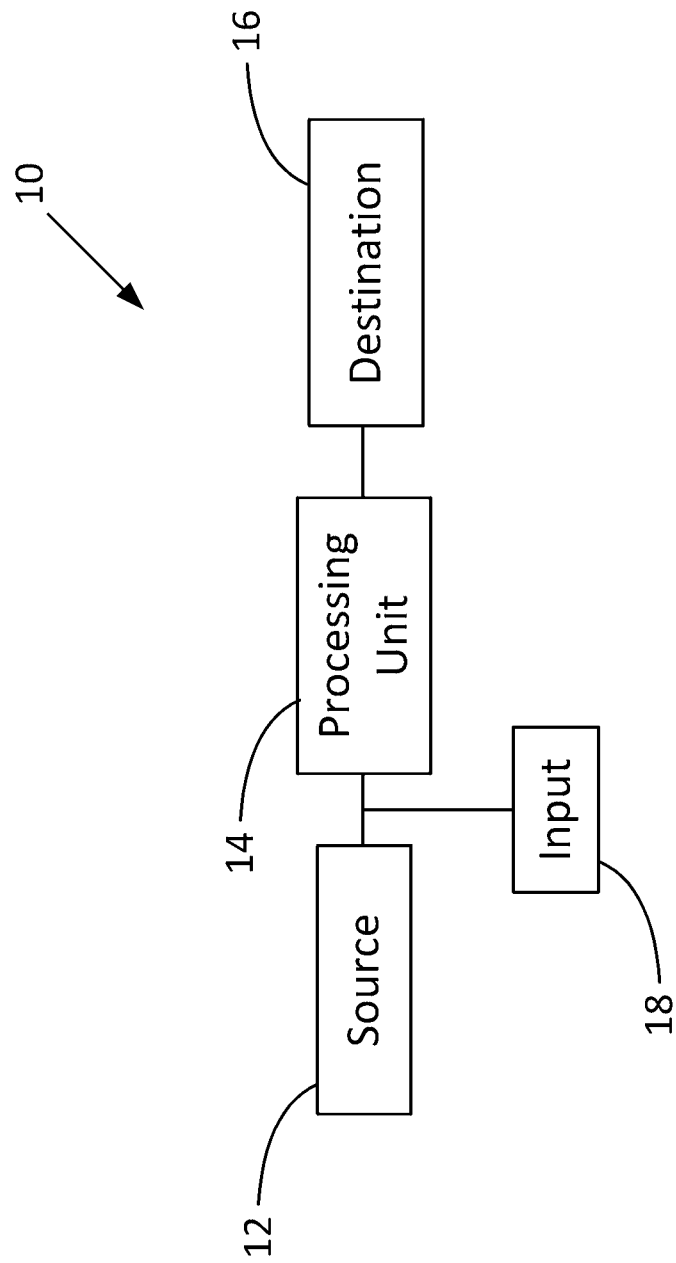
FIG. 1 is a schematic illustration of one embodiment of a system for identifying an area of interest on a surgical image.

Referring to FIG. 1, the system 10 includes at least one source 12 of surgical image data in communication with at least one processing unit 14 and at least one destination 16 for the surgical image data. The at least one source 12 of surgical image data connected to the processing unit 14 may include any device, system, or network that generates, acquires, stores, monitors, or controls surgical image data for use in generating medical images, such as still frame images or video. For example, the at least one source 12 may include an image acquisition device, such as endoscopic cameras, video endoscopes, room cameras, light cameras, and boom cameras. Likewise, the at least one source 12 may include any recording, storage, and/or archival device or system, such as traditional video cassette recorders or digital video recording devices (such as a linear tape deck or DVD recording device), image capture devices, a PACS (Picture Archiving and Communication System) computer, or a Hospital Information System. Finally, the at least one source 12 may include any other device from which surgical image data may be received, such as a patient monitor or a central computer for controlling various devices, or may simply be auxiliary inputs for connecting external devices that may supply surgical image data to the system.

Additionally, a source 12 may be a source of surgical image data that receives surgical image data from yet another source. For example, a source may be a linear tape deck that is recording live video as it supplies the video to the computer. The linear tape deck, in turn, may receive the live video from an endoscopic camera presently being used on a patient, as is further described below. As another example, a source 12 may be a processor for routing images from multiple other sources to the processing unit (i.e., a screen splitter), such as a quad image processor. The source 12 connected to the processing unit may also be a camera control unit (CCU).

The at least one processing unit 14 may include any device, system, or network that processes images generated from surgical image data. For example, the processing unit 14 may be a general processor, a computer, or a CCU, which may be integrated in a camera or may be a modular CCU external to the camera.

The at least one destination 16 for the surgical image data supplied by the at least one source 12 may include any device, system, or network that displays surgical images generated from the image data, or otherwise communicates the image data to viewers, or stores the image data. For example, the at least one destination may include any of various displays, such as, for example, a flat panel display, a plasma screen, or a computer monitor. Additionally, the at least one destination may include a recording device or a storage medium.

Further, the at least one destination 16 for the surgical image data may be located within the operating room, or it may be at a location remote from the operating room. One object of the invention is to assist all those viewing or analyzing surgical image data to identify areas of interest in the surgical image data. For example, an overlay pattern applied to surgical image data may be used by a surgeon performing the surgery to communicate with an assisting surgeon that is not present in the operating room, but who is able to view the surgical image data with the overlay pattern on a destination 16, such as a monitor, at some other remote location. Further, the overlay pattern may be applied to surgical image data displayed on a monitor located in a lecture hall or classroom for teaching purposes.

Moreover, the destination 16 may be capable of displaying surgical image data from more than one source. For example, the destination 16 may be a monitor with picture-in-picture (PIP) capabilities. In this embodiment, the user may choose to apply (or presets may set) an overlay pattern to all or some sets of surgical image data displayed on the monitor. Similarly, if there are several destinations 16 for surgical image data from several sources 12, then user may choose to apply (or presets may set) an overlay pattern to all or some sets of surgical image data sent to the destinations 16.

As illustrated in FIG. 1, the system 10 may also include at least one input 18 in communication with the at least on source 12 and/or the processing unit 14. The at least one input 18 may include any interface whereby a user to enable/disable and/or adjust the properties of the overlay pattern. In one embodiment, the input 18 may be a button or menu located on the source 12 of surgical image data, such as an endoscopic camera, itself. Alternatively, the input 18 may be a user interface that may include physical buttons for a surgeon to press, or may also include a touch-screen monitor.

Figure 2:
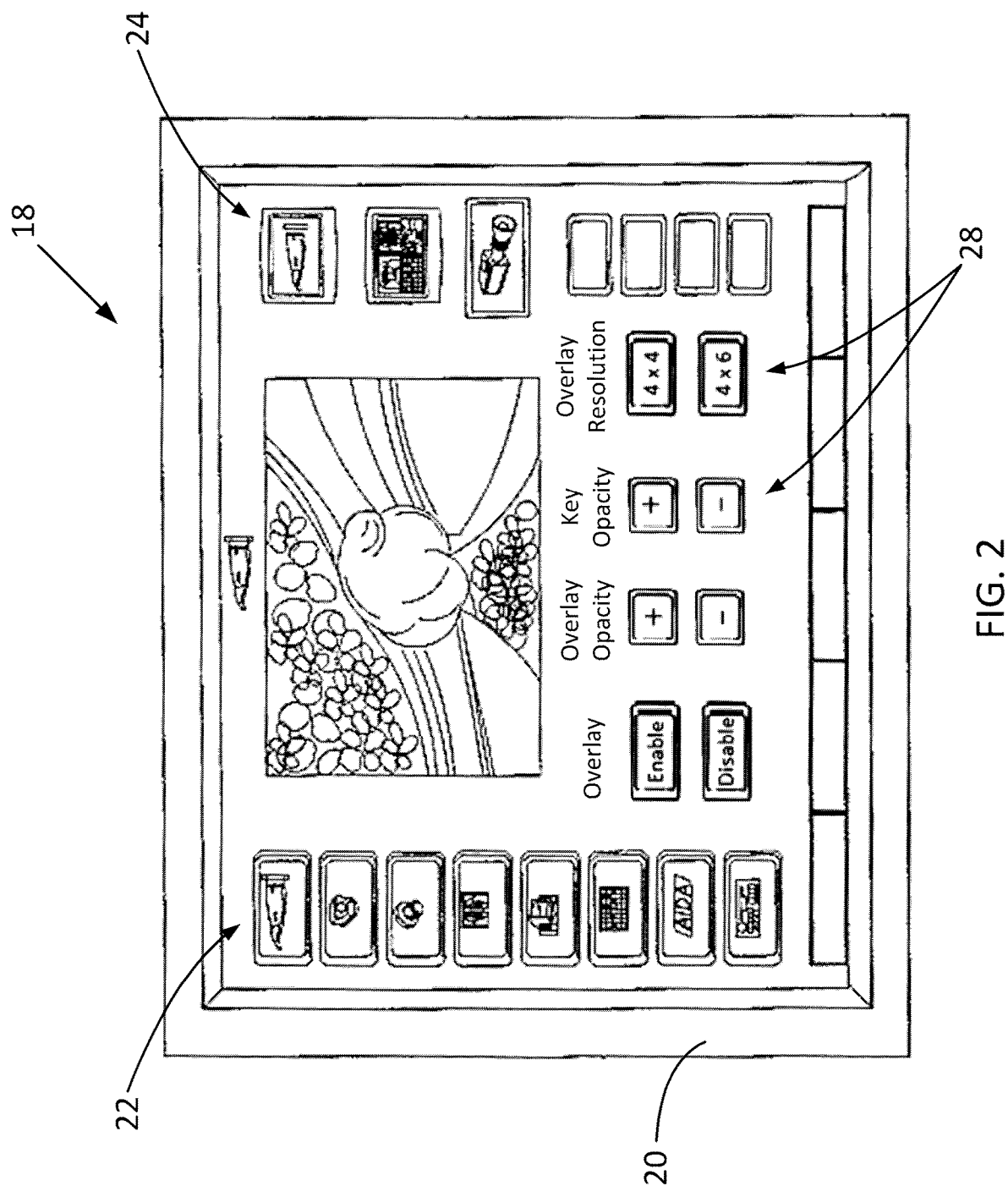
FIG. 2 is a view of an embodiment of a input for use with the system for identifying an area of interest on a surgical image as shown in FIG. 1.

In another embodiment, shown in FIG. 2, the input 18 may include one or more icons on a touchscreen 20. In this embodiment, the system 10 may include software executing on the processing unit 14 that causes the touchscreen 20 to simultaneously display several icons. The icons are sensitive to the touch of the user and will cause a command to be sent to the processing unit 14. By pressing certain source icons 22 or destination icons 24, the user can select a particular source and destination by pressing the touchscreen 20 at the locations of the icon. The user can also manipulate or alter the surgical images being displayed in the display window 26 on the touch screen in order to affect the surgical images ultimately being communicated to the destinations. For example, the touchscreen 20 may also include at least one icon 28 which allows the user to enable/disable the overlay pattern, adjust the properties of the overlay pattern, and select which surgical image data to which the overlay pattern will be applied and to which destination 16 the combined surgical image will be transmitted.

In some embodiments, the system 10 may also be configured to accept voice commands, allowing the user to vocally enable or disable the overlay pattern and adjust properties of the overlay pattern itself without having to touch the imaging device or user interface. In this embodiment, the at least one input 18 may include voice recognition software executing on said processing unit 14 for accepting voice commands, allowing the surgeon to vocally enable or disable the overlay and adjust properties of the overlay itself without having to physically touch the source 12, processing unit 14 or input 18 themselves.

In some further embodiments, the input 18 may include accelerometer data from the camera head or image motion vector detection. The overlay pattern may be automatically enabled or disabled or the properties of the overlay pattern may be adjusted in response to the input of this data.

The input 18 may also include preset data saved by the user that will act on the processing unit 14 to enable/disable the overlay pattern at certain times as preset by the user. The preset data may also include the preferred type of overlay pattern and/or the properties of the overlay pattern the user desires to be sent to the destination 16.

Figure 5:
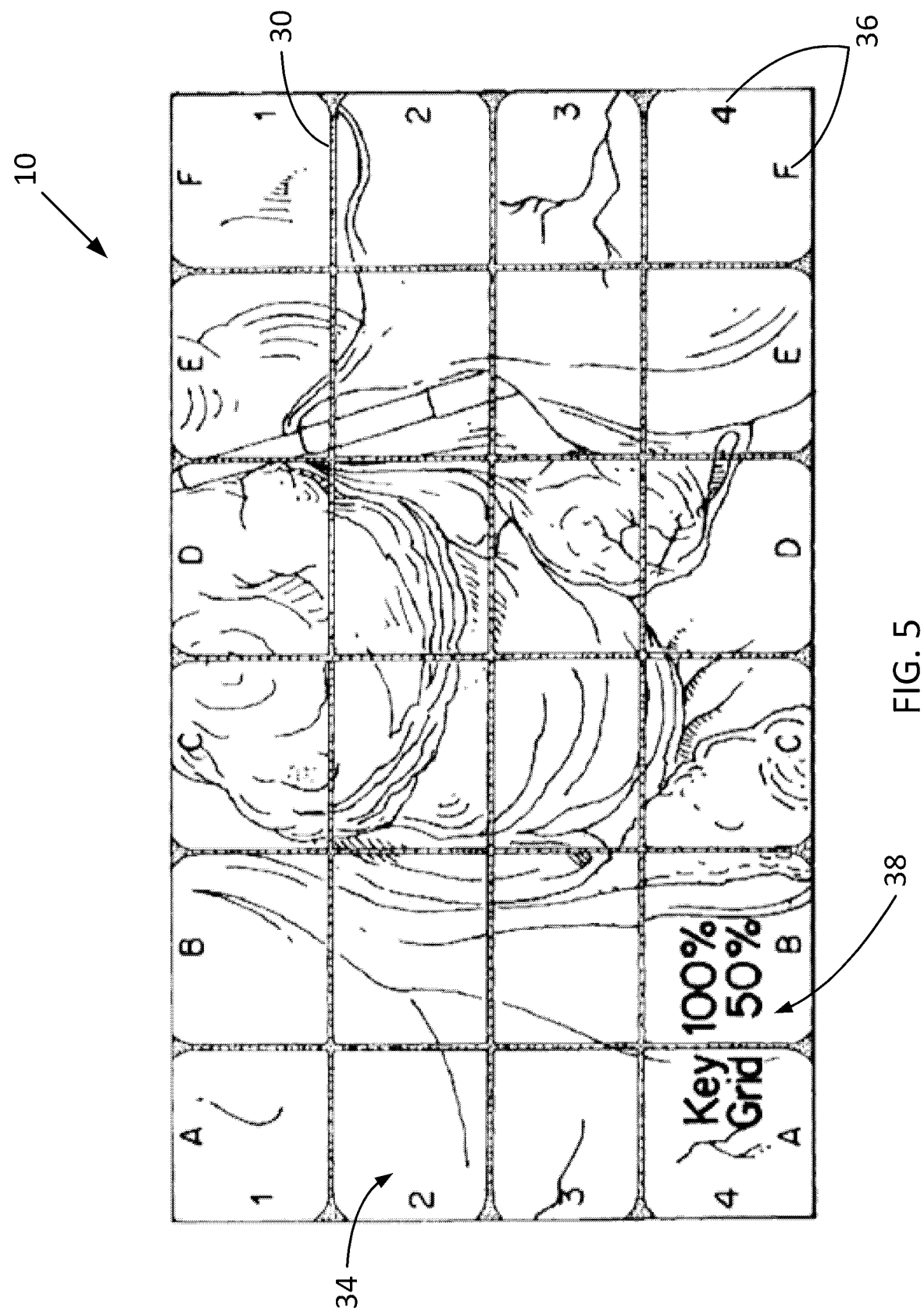
FIG. 5 is a view of an overlay pattern combined in the form of a grid at 50% opacity and a key at 100% opacity, combined with surgical image data, for use with the system for identifying an area of interest on a surgical image as shown in FIG. 1.
Figure 6:
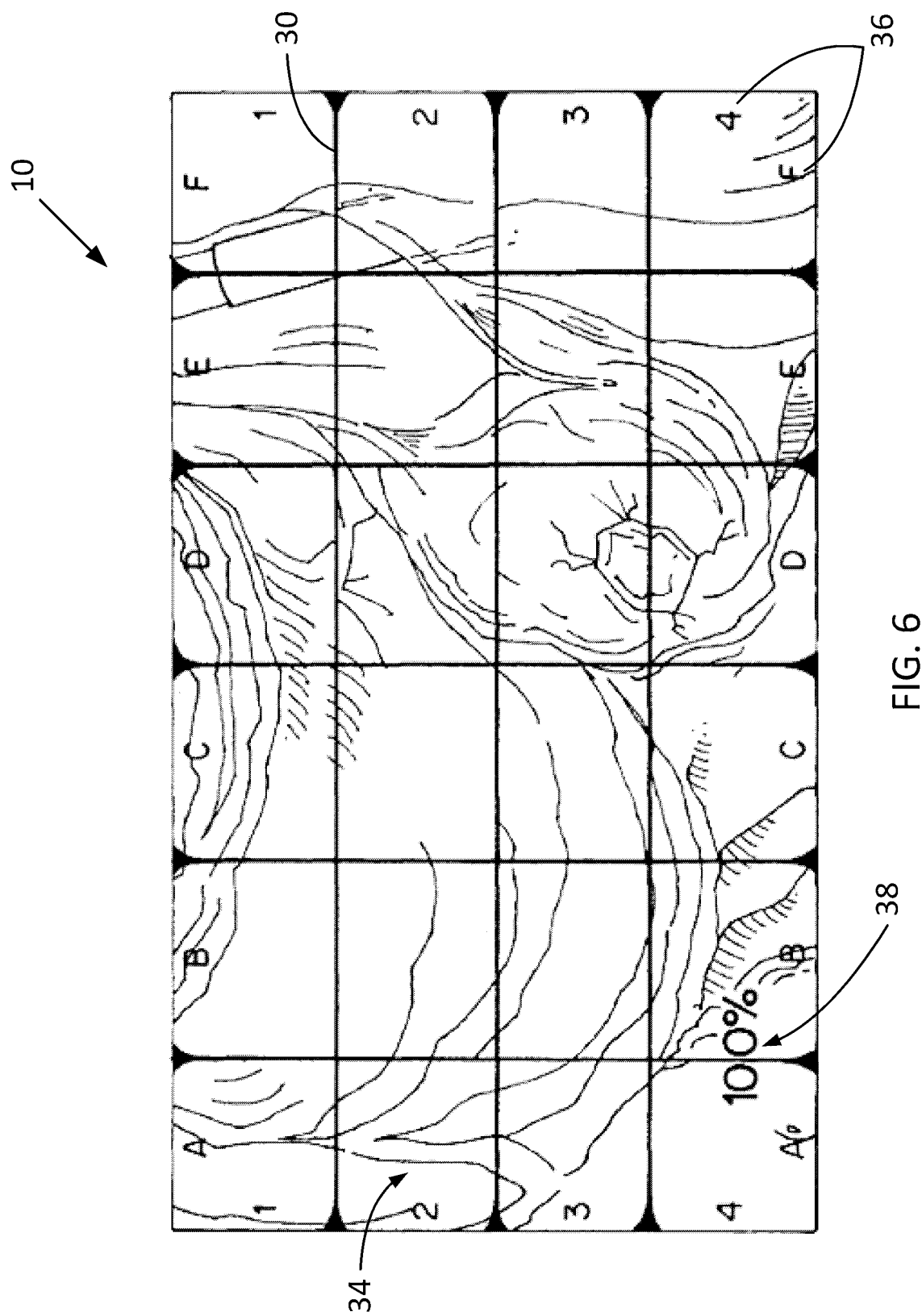
FIG. 6 is a view of an overlay pattern in the form of a grid with a key, both at 100% opacity, combined with surgical image data that has been zoomed in, for use with the system for identifying an area of interest on a surgical image as shown in FIG. 1.
Figure 7:
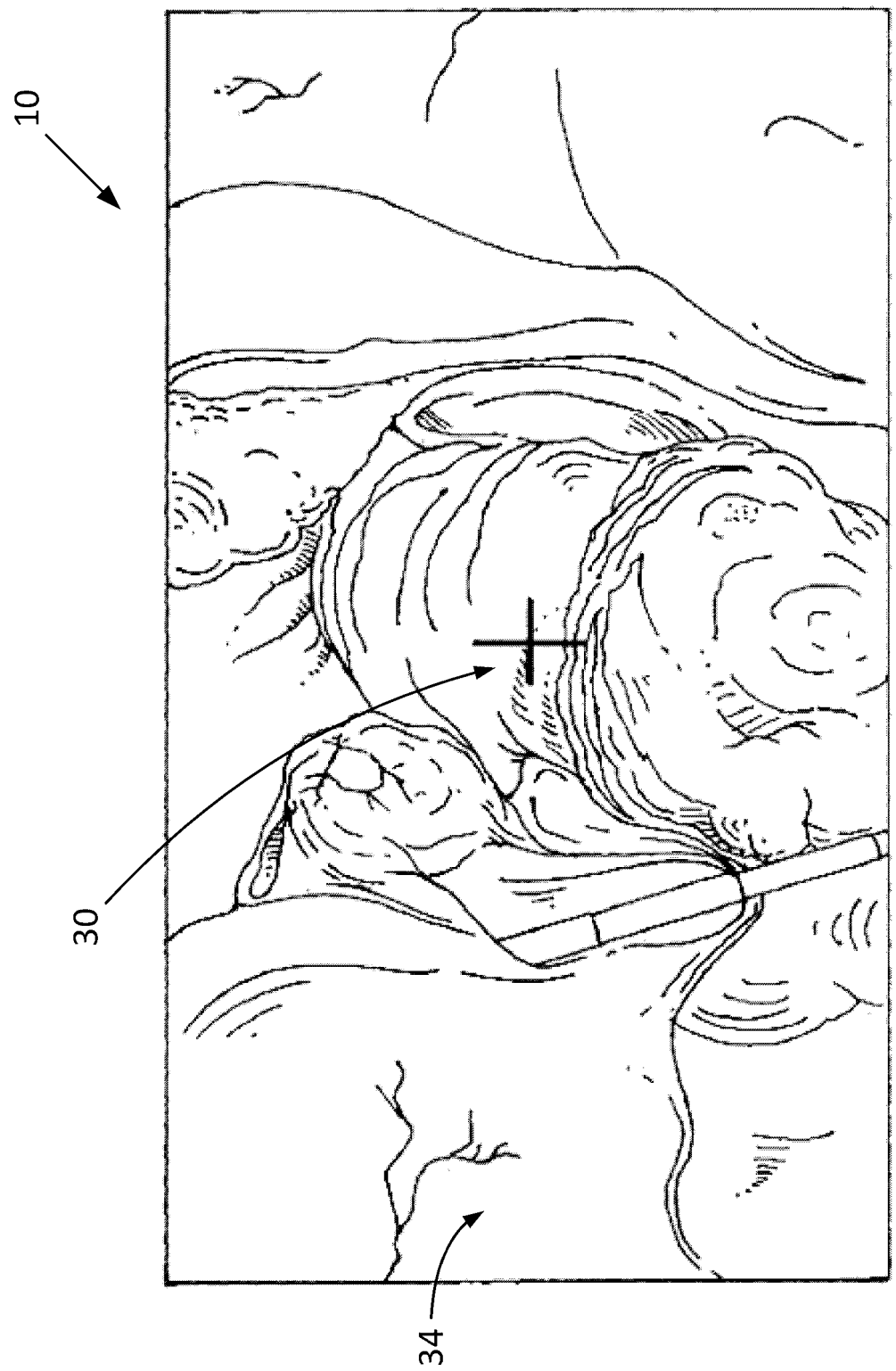
FIG. 7 is a view of an overlay pattern in the form of a centered crosshairs, combined with surgical image data, for use with the system for identifying an area of interest on a surgical image as shown in FIG. 1.
Figure 8:
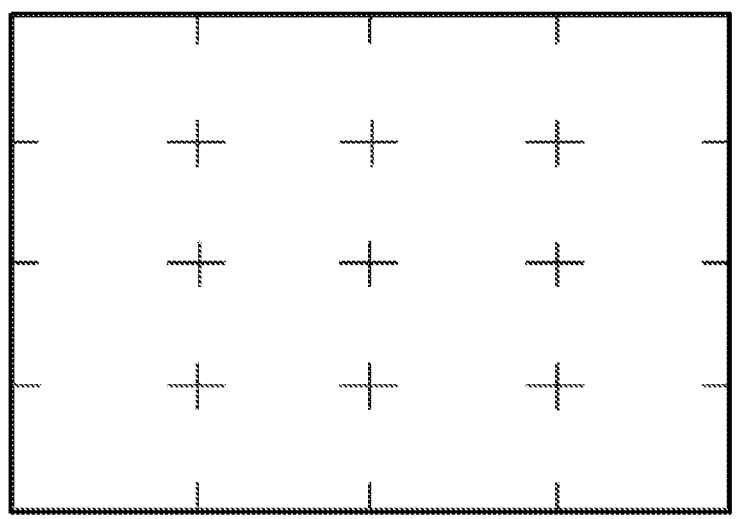
FIG. 8 is a view of an overlay pattern for use with the system for identifying an area of interest on a surgical image as shown in FIG. 1.
Figure 9:
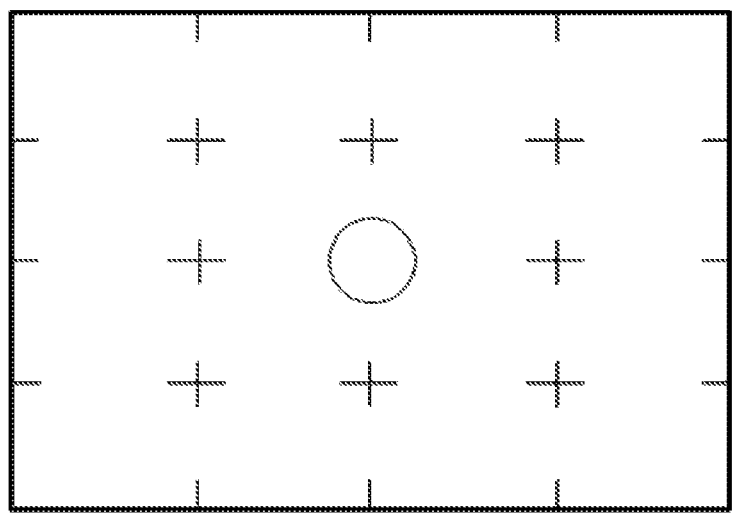
FIG. 9 is a view of an overlay pattern for use with the system for identifying an area of interest on a surgical image as shown in FIG. 1.
Figure 10:
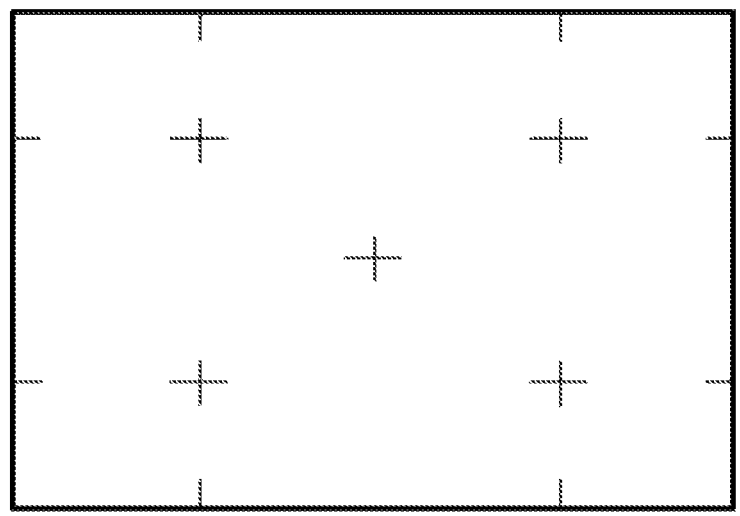
FIG. 10 is a view of an overlay pattern for use with the system for identifying an area of interest on a surgical image as shown in FIG. 1.

As shown in FIGS. 3 and 7-21, the overlay pattern 30 may be provided in any number of designs, which may be set by the user. For example, as shown in FIGS. 3-6, the overlay pattern 30 may be a grid. In addition, as shown in FIG. 7, the overlay pattern 30 may include a single crosshairs placed at the center of the surgical image as displayed. In other embodiments, the overlay pattern may be one or more hash marks or crosshairs overlaid across a portion of the surgical image, the entire surgical image, or at the edges of the image. The overlay may also be separated into quadrants, with any number of circles, ovals hash marks or any combination thereof within the quadrants. The overlay may also be one or more circles, ovals or other shapes.

The desired overlay pattern 30 may be chosen by the user through an input 18, some examples of which are described above. For example, the source 12, such as an endoscopic camera, may include buttons for selecting and setting a desired overlay pattern 30. The user may also chose to apply the overlay pattern 30 to one or all of the sources 12 of surgical image data 34. Once the overlay pattern 30 is selected, the surgical image data 34 from the one or more selected sources 12 is combined with the overlay pattern 30 in the processing unit 14 and the combined surgical image is transmitted to the one or more selected destinations 18.

Figure 3:
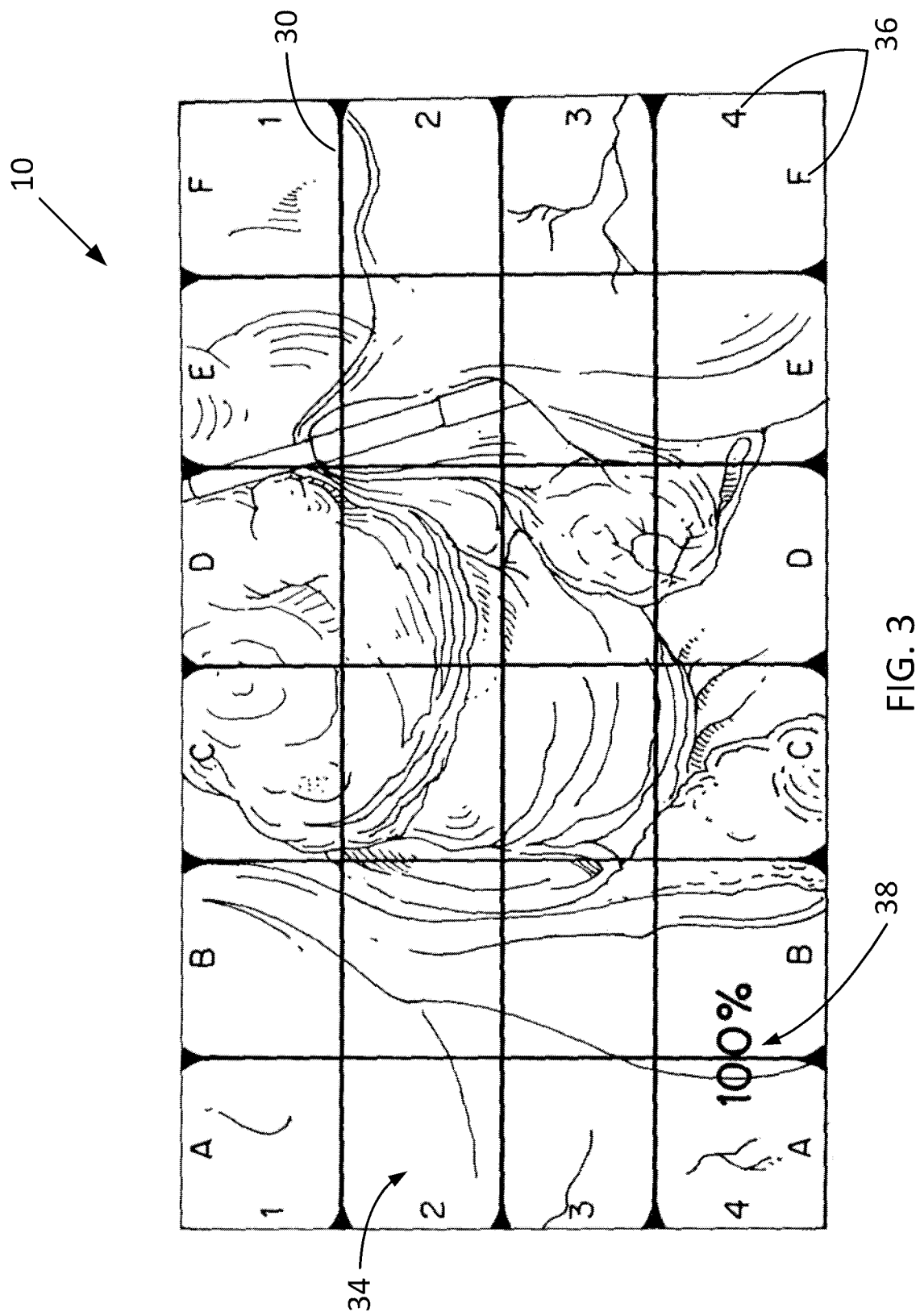
FIG. 3 is a view of an overlay pattern in the form of a grid with a key, both at 100% opacity, combined with surgical image data, for use with the system for identifying an area of interest on a surgical image as shown in FIG. 1.

In one embodiment, the overlay pattern is applied to live surgical images, in real time. For example, as shown in FIG. 3, the combined surgical image data 34 and overlay pattern 30 may be transmitted to a display 32. The display may be located in the operating room and/or it may be located somewhere remote from the operating room for viewing by other surgeons assisting in the surgery or by students observing the surgery for educational purposes.

Further, the overlay pattern 30 may be applied to surgical image data 34 that has been recalled from an image archive, such as on a storage medium. The applied overlay pattern 30 may also be maintained on captured surgical image data 34 that is subsequently saved to an archive and may be recalled later for viewing on a display.

The overlay pattern 30 may be applied to the surgical image data at a "fixed" position, meaning that the overlay 30 will be applied at a fixed position with respect to the displayed image, i.e., centered on the surgical image. However, the user may adjust the surgical image data 34 separately with respect to the overlay pattern 30. In operation, the user views the surgical image data with the overlay pattern 30 on a display 32 and adjusts the image captured by the source 12 (i.e., a camera) until the particular area of interest is located at or near an identifiable region of the overlay pattern 30. Using the embodiment shown in FIG. 7, the surgeon will adjust the field of view of the camera until the area of interest is centered at the crosshairs. This allows the surgeon to unequivocally "point" to the area of interest, simply by adjusting the camera.

Figure 11:
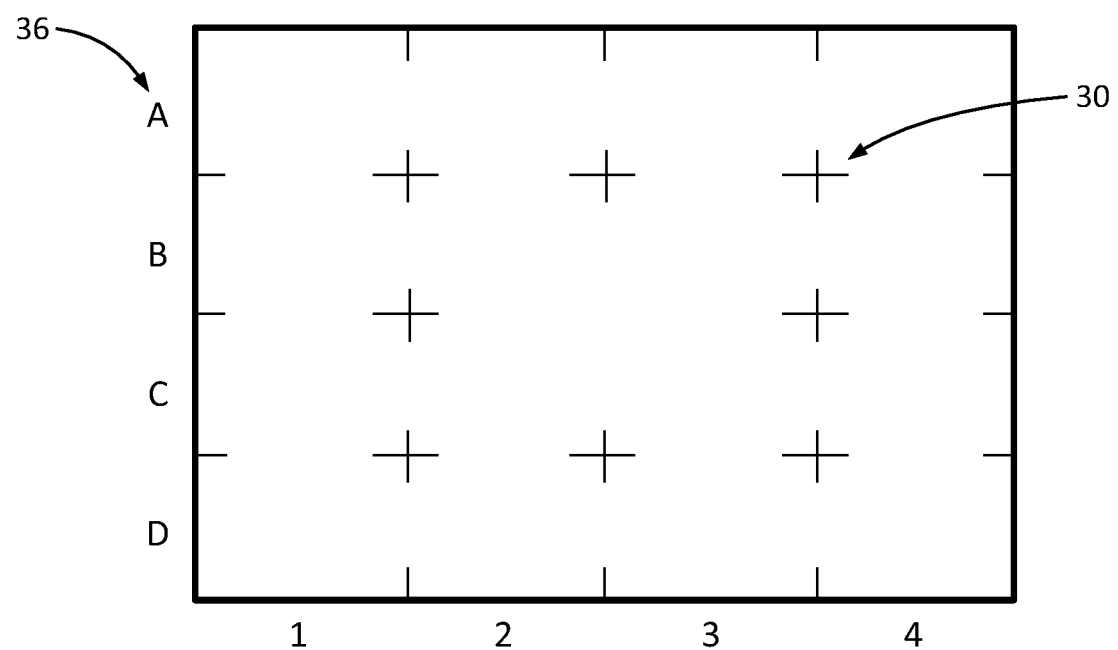
FIG. 11 is a view of an overlay pattern for use with the system for identifying an area of interest on a surgical image as shown in FIG. 1.
Figure 12:
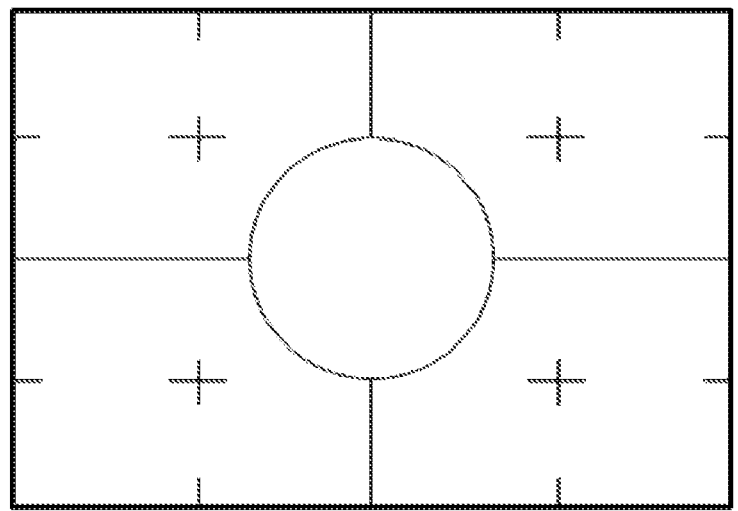
FIG. 12 is a view of an overlay pattern for use with the system for identifying an area of interest on a surgical image as shown in FIG. 1.
Figure 13:
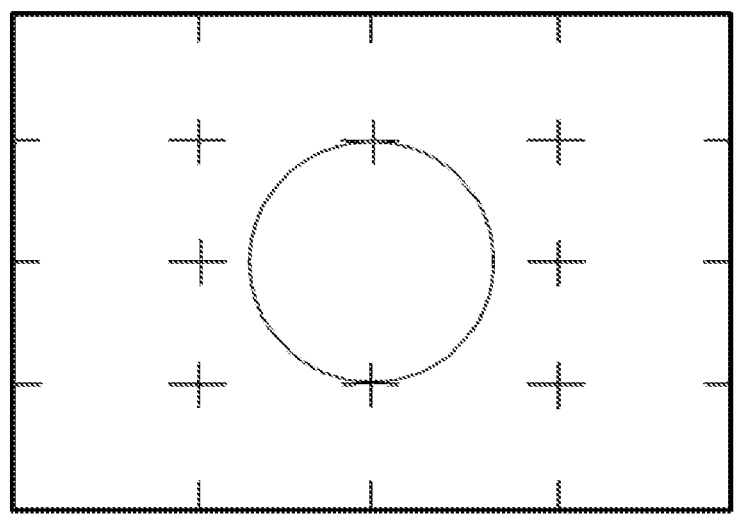
FIG. 13 is a view of an overlay pattern for use with the system for identifying an area of interest on a surgical image as shown in FIG. 1.
Figure 16:
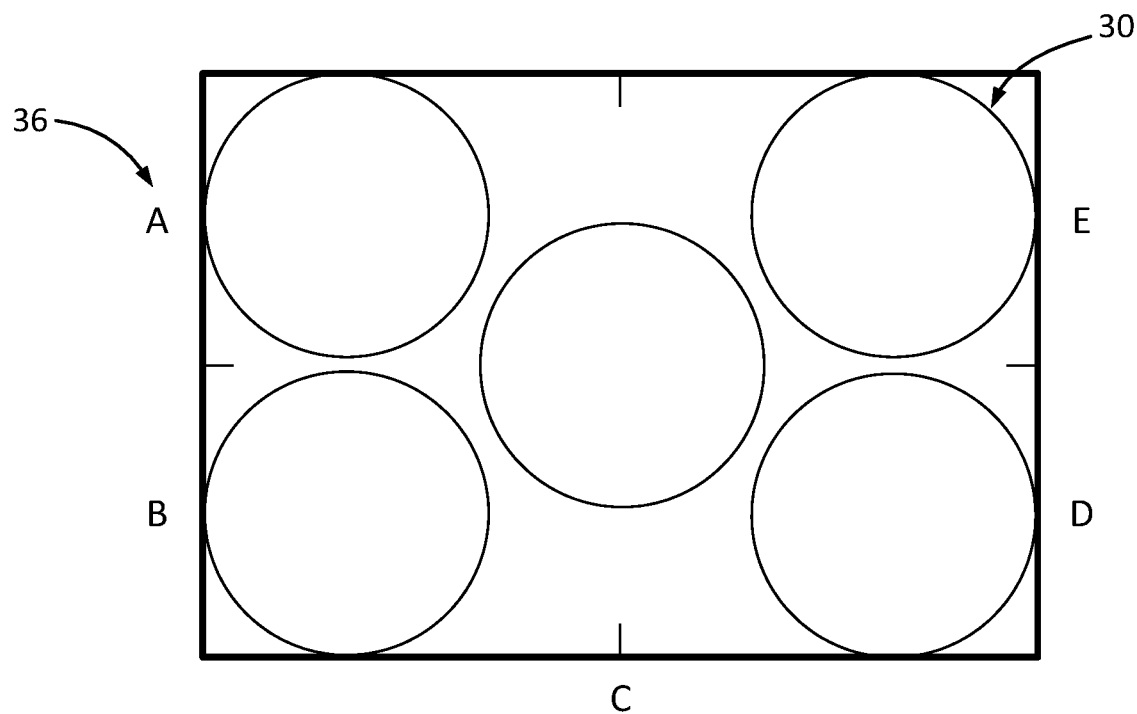
FIG. 16 is a view of an overlay pattern for use with the system for identifying an area of interest on a surgical image as shown in FIG. 1.
Figure 17:
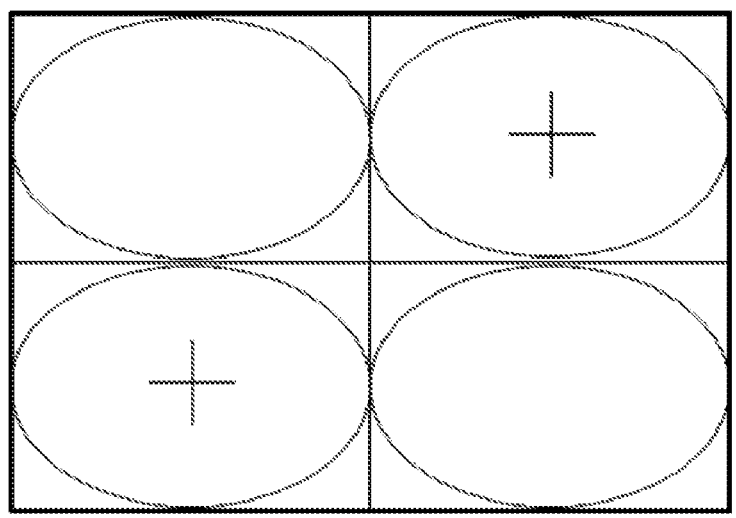
FIG. 17 is a view of an overlay pattern for use with the system for identifying an area of interest on a surgical image as shown in FIG. 1.
Figure 18:
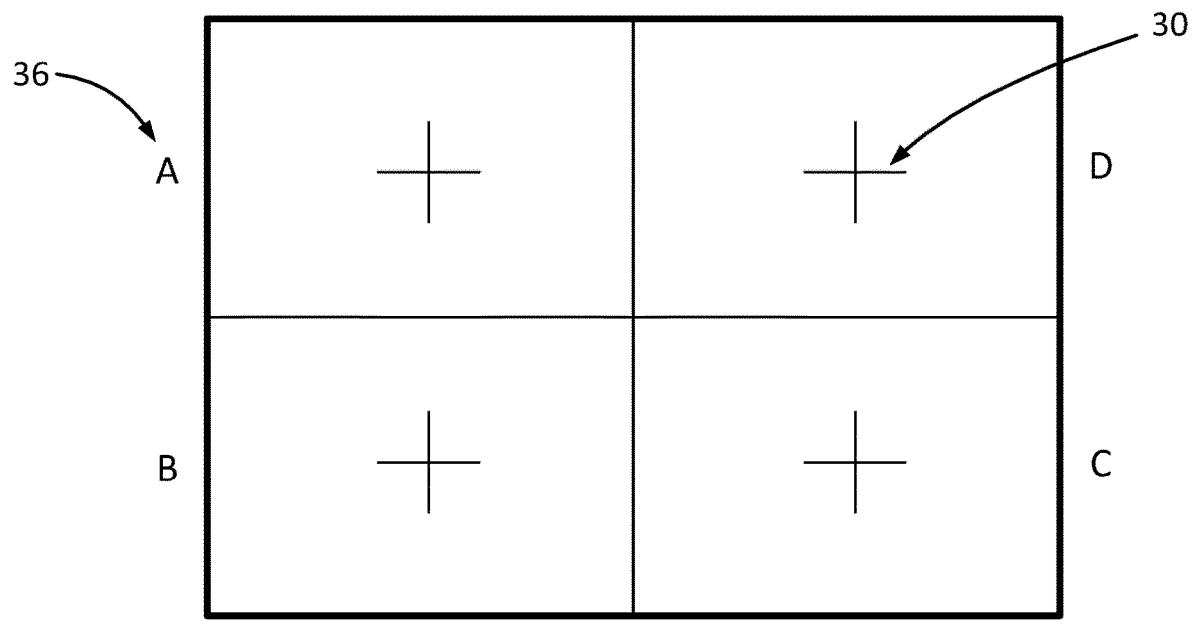
FIG. 18 is a view of an overlay pattern for use with the system for identifying an area of interest on a surgical image as shown in FIG. 1.
Figure 19:
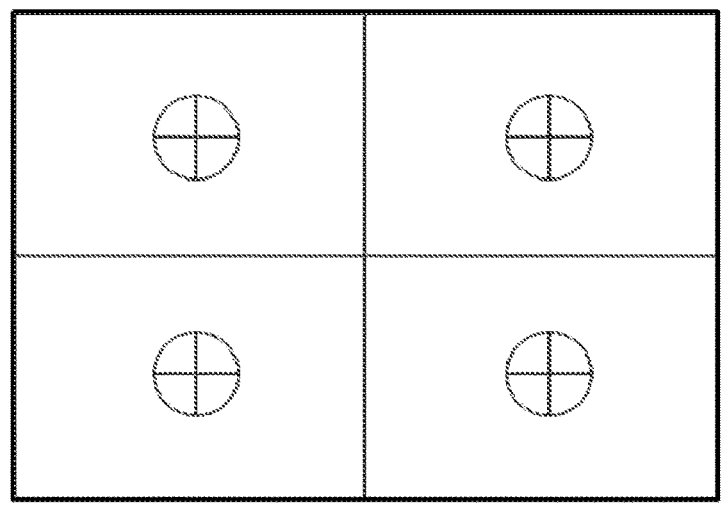
FIG. 19 is a view of an overlay pattern for use with the system for identifying an area of interest on a surgical image as shown in FIG.
Figure 20:
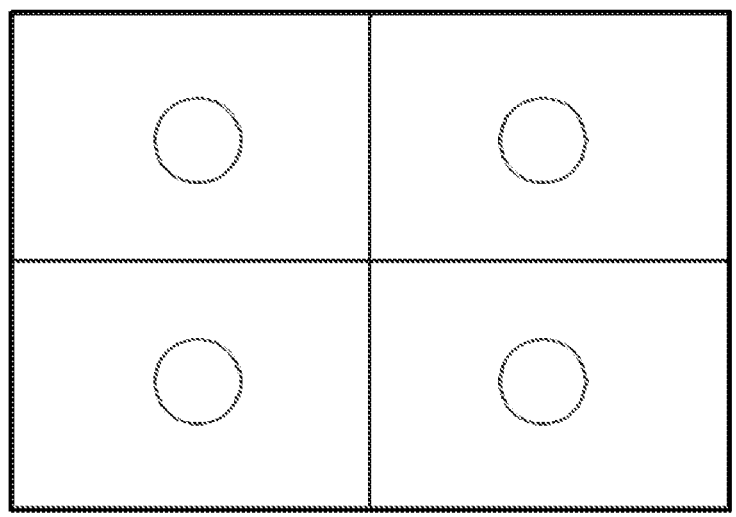
FIG. 20 is a view of an overlay pattern for use with the system for identifying an area of interest on a surgical image as shown in FIG.
Figure 21:
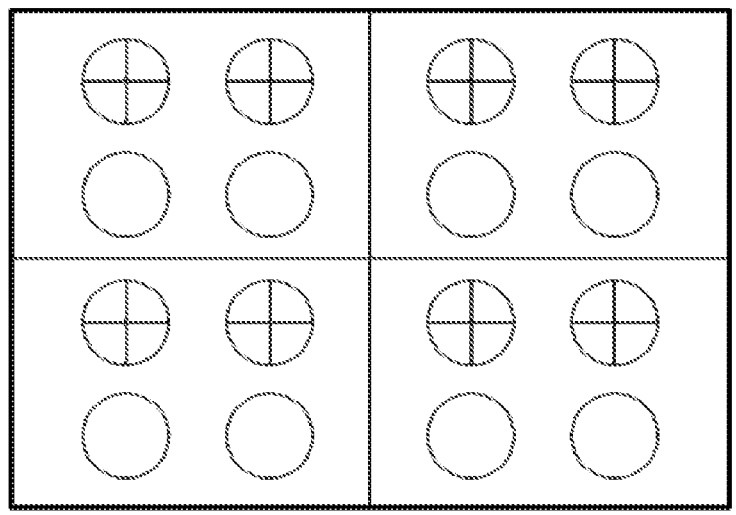
FIG. 21 is a view of an overlay pattern for use with the system for identifying an area of interest on a surgical image as shown in FIG. 1.

The overlay pattern may also include a key 36 for assisting the user in identifying and discussing areas or portions of the overlay pattern 30, and, in turn, identifying and discussing an area of interest on the underlying surgical image data 34. In one example, the key 36 may include alphanumeric labels or coordinates. For example, as shown in FIG. 3 the rows and columns of a grid overlay may be labeled with letters and numbers—the vertical axis labeled with letters and the horizontal axis labeled with numbers (or vice versa) allowing reference to an area of the surgical image with a simple letter-number combination (e.g. "C3" or "D2", etc.). In another embodiment, if the overlay pattern 30 comprises hash-marks as shown in FIG. 11, the hash marks may be labeled with coordinates. As shown in FIGS. 16 and 18, the quadrants or other defining shapes may be individually labeled with an alphanumeric key 36.

Certain properties of the overlay 30 and key 36 may be adjustable, including, but not limited to, the resolution (i.e., number of rows by number of columns, number of circles, etc.) of the overlay, the opacity of the overlay pattern 30 and/or key 36, the distribution of the opacity of the overlay pattern 30 and/or key 36, the color of the overlay 30 and/or key 36, the brightness of the overlay 30 and/or key 36, the thickness of the lines of the overlay pattern 30, the size of the font of the key 36, etc. The user may choose to enable the overlay pattern and set its properties prior to the start of the surgical procedure, or the overlay may be enabled/disabled and the properties may be adjusted at any time during the surgical procedure.

Figure 4:
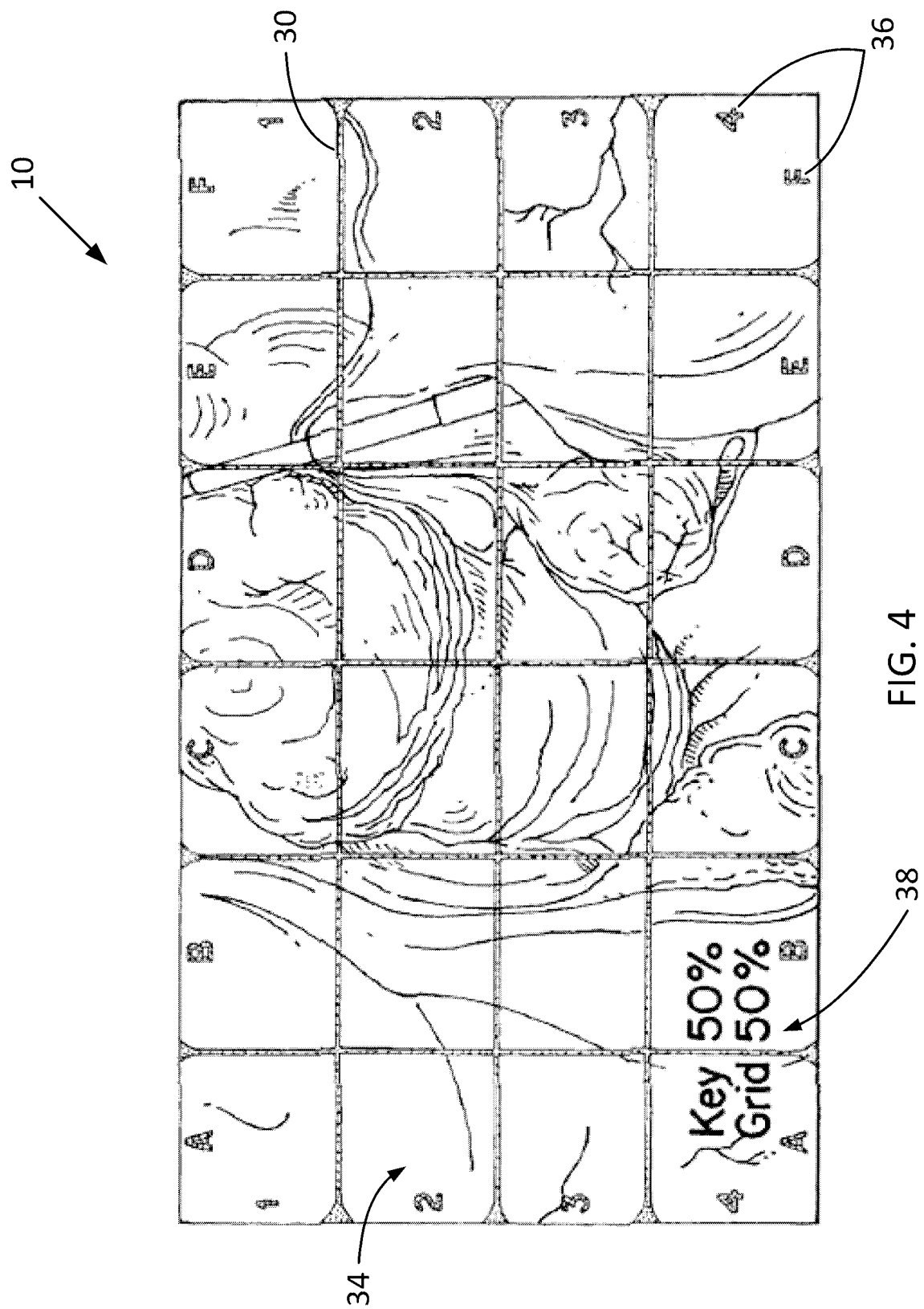
FIG. 4 is a view of an overlay pattern in the form of a grid with a key, both at 50% opacity, combined with surgical image data, for use with the system for identifying an area of interest on a surgical image as shown in FIG. 1.

In one example, the overlay pattern 30 and key 36 can be applied to the surgical image in varying levels of opacity. The overlay may also include an indicator 38, which may display certain properties of the overlay 30 as set by the user. For example, FIG. 3 illustrates the overlay 30 as a grid and key 36 applied at 100% opacity. FIG. 4 illustrates the overlay 30 and the key 36 both applied at 50% opacity. The properties of the overlay 30 can be constant or can vary across the display 32. For example, the overlay pattern 30 can be more opaque at the edges of the display 32 and gradually become more transparent toward the center of the display 32.

In a further embodiment, the adjustable properties of the overlay pattern and coordinates may be adjusted independently of one another. For example, as shown in FIG. 5, the overlay may be set to 50% opacity whereas the key 36 may be maintained at 100% opacity.

Various properties of the camera control unit (CCU) may also be changed so as to effect a change in the surgical image data 34 at and/or around certain coordinates or a region of the overlay 30 identified by the user. For example, the brightness, contrast, color, or zoom of the surgical image data 34 may be adjusted at and/or around the coordinates or region identified. The coordinates or region of the overlay 30 may be identified via an input 18, for example by button press on the source 12 or by touching an icon or the display window 26 of a touchscreen 20. The system 10 may also be configured to include voice recognition of certain regions or coordinates of the overlay pattern 30 to change the properties of the CCU.

Moreover, the zoom level of the surgical image data 34 itself may be adjusted independent of the overlay pattern 30. The resolution of the overlay pattern 30 will remain the same, while the surgical image data 34 is zoomed in or out. For example, FIG. 6 illustrates a zoomed-in version of the surgical image data 34 of FIG. 3, where the resolution of the grid overlay pattern remains constant (4 rows by 6 columns).

The user may set or adjust the properties of the overlay pattern 30 and/or the key 36 at the beginning of, or during, a surgical procedure. For example, the user may select a grid overlay, choose the number of columns and rows, and set the color all at prior to commencing a surgical procedure. The user may also establish presets to which the overlay 30 will default. In one embodiment shown in FIGS. 1-7, the resolution of the grid overlay is four rows by six columns. However, other grid overlay resolutions are contemplated, such as 4×4. The overlay can be of a varying number or a fixed number of columns, rows, quadrants, etc.

Figure 14:
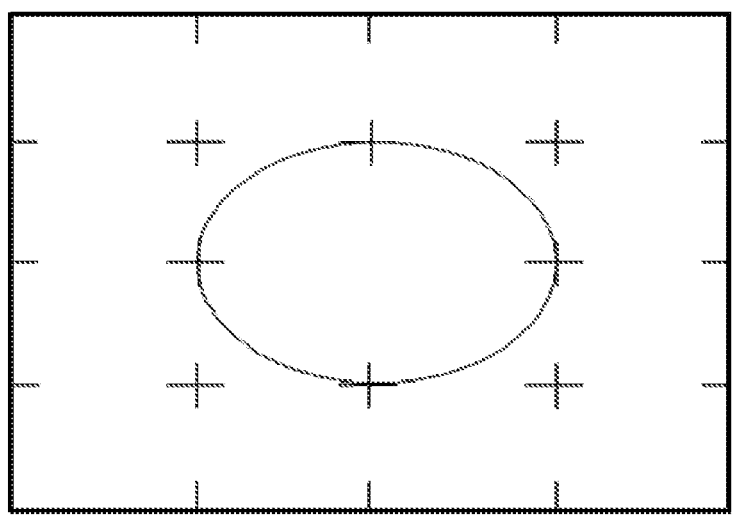
FIG. 14 is a view of an overlay pattern for use with the system for identifying an area of interest on a surgical image as shown in FIG. 1.
Figure 15:
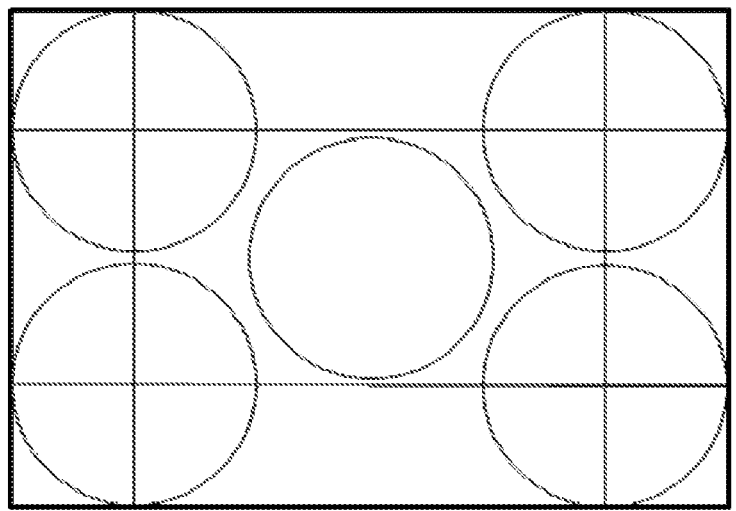
FIG. 15 is a view of an overlay pattern for use with the system for identifying an area of interest on a surgical image as shown in FIG. 1.

Additionally, the overlay pattern and/or resolution may be preset or chosen by the surgeon in accordance with the aspect ratio of the display monitors. For example, the surgeon may chose a standard definition (SD) display having a 4×3 aspect ratio and the overlay pattern would be chosen or adjusted accordingly. The surgeon may also chose a high definition (HD) display having a 16×9 aspect ratio and the overlay pattern would be chose or adjusted accordingly. Overlay patterns incorporating ovals, such as the pattern shown in FIG. 15, are well suited for HD displays whereas overlay patterns incorporating circles, such as the pattern shown in FIG. 14, are well suited for SD displays.

In a further embodiment, the system 10 may automatically enable the overlay if a motion vector detector (as an input 18) senses a still image for a certain period of time. Conversely, the system 10 may automatically disable the overlay if a motion vector detector senses a moving image for a certain period of time. Further, the system 10 may automatically "time out" after the overlay has been enabled for a preset period of time, or "time-out" if the surgical image has been still for a certain period of time.

When the overlay is enabled or disabled, either by automatic sensing, "time-out" or by direct input from the user, the overlay could be programmed to either immediately appear at 100% opacity or immediately disappear. Alternatively, the overlay could be programmed to gradually appear or disappear by gradual increase or decrease in opacity. These properties will be discussed further below.

It should be understood that the foregoing is illustrative and not limiting, and that obvious modifications may be made by those skilled in the art without departing from the spirit of the invention.

What is claimed is:

1. A system for identifying an area of interest on a surgical image, comprising:
    an endoscopic camera configured to generate surgical image data;
    a processor configured to receive and process said surgical image data from said endoscopic camera;
    an accelerometer configured to generate accelerometer data indicative of movement of said endoscopic camera over a period of time;
    said processor including a non-transitory computer-readable storage medium on which a software is stored, said software configured to change a predefined overlay pattern between an enabled state and a disabled state in response to accelerometer data received from said accelerometer;
    said processor configured to adjust at least one property of said overlay pattern, and said processor configured to independently adjust a zoom level of said overlay pattern and a zoom level of said surgical image data;
    said overlay pattern selected from a group consisting of a grid, crosshairs, quadrants, hash marks, a circle, and an oval;
    said software configured to adjust said surgical image data such that an area of interest is located near a region of said overlay pattern;
    said software further configured to adjust at least one property of said surgical image data generated by said endoscopic camera in and around said area of interest; and
    a display controlled by said processor for displaying said surgical image data and said overlay pattern;
    wherein in said enabled state said overlay pattern is displayed on said display, and in said disabled state said overlay pattern is not displayed on said display.

2. The system of claim 1 wherein said surgical image data is selected from the group consisting of: video data, still frame data and combinations thereof.

3. The system of claim 1 further comprising a storage device configured to save said surgical image data and said overlay pattern.

4. The system of claim 1 wherein said overlay pattern further includes a key configured to identify one or more regions of said overlay pattern.

5. The system of claim 1 wherein said overlay pattern comprises a grid.

6. The system of claim 1 wherein said overlay pattern comprises crosshairs.

7. The system of claim 6 wherein one of said crosshairs is centered on said surgical image data when displayed.

8. The system of claim 1 wherein said overlay pattern comprises quadrants.

9. The system of claim 1 wherein said overlay pattern comprises one or more hash marks.

10. The system of claim 9 wherein at least some of said one or more hash marks are located on at least one edge of said surgical image data when displayed.

11. The system of claim 1 wherein said overlay pattern comprises a circle.

12. The system of claim 1 wherein said overlay pattern comprises an oval.

13. The system of claim 1 wherein said at least one property of said overlay pattern is chosen from the group consisting of: brightness, contrast, opacity, resolution and color.

14. The system of claim 1, wherein said endoscopic camera includes one or more buttons, and wherein said at least one property of said overlay pattern can be adjusted via said one or more buttons.

15. The system of claim 1, further comprising a touchscreen, wherein said at least one property of said overlay pattern can be adjusted via said touchscreen.

16. The system of claim 1, further comprising a voice recognition software stored on said non-transitory computer-readable storage medium, wherein said at least one property of said overlay pattern can be adjusted via the voice recognition software.

17. The system of claim 1 wherein said display is configured to present said surgical image data generated by said endoscopic camera or said overlay pattern as a picture-in-picture.

18. The system of claim 1, wherein said software is configured to change said overlay pattern between said enabled state and said disabled state by changing opacity of said overlay pattern.

19. The system of claim 1, wherein said software is configured to immediately change said overlay pattern between said enabled state and said disabled state.

20. The system of claim 1, wherein said software is configured to gradually change said overlay pattern between said enabled state and said disabled state.

21. The system of claim 1, wherein said software is configured to change from said disabled state to said enabled state when said accelerometer data indicates no movement of said endoscopic camera over said period of time.

22. The system of claim 1, wherein said software is configured to change from said enabled state to said disabled state when said accelerometer data indicates movement of said endoscopic camera over said period of time.

* * * * *